United States Patent [19]

Brown

[11] Patent Number: 4,571,398
[45] Date of Patent: Feb. 18, 1986

[54] CYTOSINE DERIVATIVES HAVING HISTAMINE H$_2$-ANTAGONIST ACTIVITY

[75] Inventor: Thomas H. Brown, Tewin, England

[73] Assignee: Smith Kline & French Laboratories Limited, Welwyn Garden City, England

[21] Appl. No.: 622,411

[22] Filed: Jun. 20, 1984

[30] Foreign Application Priority Data

Jul. 9, 1983 [GB] United Kingdom ............... 8318638

[51] Int. Cl.$^4$ ................ A61K 31/505; C07D 401/12
[52] U.S. Cl. .................................... 514/259; 514/212; 514/274; 260/243.3; 544/284; 544/286; 544/317
[58] Field of Search ............ 544/317, 284, 286; 424/251; 514/274, 212, 259; 260/243.3

[56] References Cited

U.S. PATENT DOCUMENTS

| | | | |
|---|---|---|---|
| 3,932,644 | 1/1976 | Durant et al. | 424/251 |
| 4,234,588 | 11/1980 | Brown et al. | 544/331 |
| 4,374,836 | 2/1983 | Yellin et al. | 424/251 |
| 4,385,058 | 5/1983 | Cooper et al. | 544/321 |
| 4,463,005 | 7/1984 | Jones et al. | 424/251 |

FOREIGN PATENT DOCUMENTS 2030979 4/1980 United Kingdom .

OTHER PUBLICATIONS

Derwent Abstract 38240c (EP 13,071) Jul. 9, 1980.

*Primary Examiner*—Glennon H. Hollrah
*Assistant Examiner*—James H. Turnipseed
*Attorney, Agent, or Firm*—Joan S. Keps; Richard D. Foggio; Alan D. Lourie

[57] ABSTRACT

This invention relates to cytosine derivatives which have histamine H$_2$-antagonist activity. A specific compound of this invention is 4-[3-(3-(piperidinomethyl)-phenoxy)propylamino]-pyrimidin-2-thione.

21 Claims, No Drawings

CYTOSINE DERIVATIVES HAVING HISTAMINE H₂-ANTAGONIST ACTIVITY

This invention relates to cytosine derivatives, and in particular to such derivatives comprising a Mannich group. This invention further relates to processes for their preparation, pharmaceutical compositions containing them and their use as histamine H$_2$-antagonists.

Histamine, a physiologically active compound endogenous in mammals, exerts its action by interacting with certain sites called receptors. One type of receptor is known as a histamine H$_1$-receptor (Ash and Schild, Brit. J. Pharmac. Chemother. 27 427 (1966)) and the actions of histamine mediated through these receptors are blocked by drugs commonly called "antihistamines" (histamine H$_1$-antagonists) a common example of which is mepyramine. A second type of histamine receptor is known as the H$_2$-receptor (Black et al. Nature 1972, 236, 385). These receptors are not blocked by mepyramine but are blocked by burimamide. Compounds which block these histamine H$_2$-receptors are called histamine H$_2$-antagonists.

Histamine H$_2$-antagonists are useful in treating disease conditions caused by the biological effects of histamine mediated through H$_2$-receptors, for example, as inhibitors of gastric acid secretion, in the treatment of inflammation mediated through histamine H$_2$-receptors and as agents which act on the cardiovascular system, for example, as inhibitors of effects of histamine on blood pressure mediated through histamine H$_2$-receptors.

Cimetidine is an example of a histamine H$_2$-antagonist. Cimetidine has been shown to be useful in the treatment of duodenal, gastric, recurrent and stomal ulceration, and reflux oesophagitis and in the management of patients who are at high risk from haemorrhage of the upper gastrointestinal tract.

In some physiological conditions the biological actions of histamine are mediated through both histamine H$_1$- and H$_2$-receptors and blockade of both types of receptors is useful. These conditions include inflammation mediated by histamine, for example skin inflammation, and those hypersensitivity responses due to the action of histamine at H$_1$- and H$_2$-receptors, for example allergies.

Accordingly the present invention provides a compound of the formula (I):

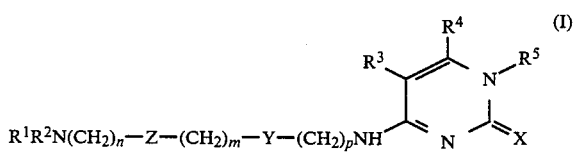

or a pharmaceutically acceptable salt thereof, wherein:
R$^1$ and R$^2$ are independently hydrogen, C$_{1-6}$alkyl, aryl(C$_{1-6}$)alkyl, heteroaryl(C$_{1-6}$)alkyl, C$_{3-10}$-cycloalkyl, hydroxy(C$_{2-6}$)alkyl, halo(C$_{2-6}$)alkyl. (wherein said hydroxy and halo groups are not substituted on the carbon atom adjacent to the nitrogen atom); or
R$^1$ and R$^2$ together represent —(CH$_2$)$_q$— wherein q is 4 to 7 to form together with the nitrogen atom to which they are attached a 5–8 membered saturated ring;
n is an integer from 1 to 6;
Z is 2,5-furanyl, 2,5-thienyl, 2,4-pyridyl wherein the R$^1$R$^2$N(CH$_2$)$_n$ group is in the 4-position, or 1,3- or 1,4-phenylene;
m is one; or if Z is pyridyl or phenylene m may also be zero;
Y is oxygen, sulphur or methylene; or if Z is furanyl or thienyl Y may also be a bond;
p is two, three or four;
X is oxygen or sulphur; and
R$^3$, R$^4$ and R$^5$ independently represent hydrogen or C$_{1-6}$alkyl, or R$^3$ and R$^4$ together represent a butadien-1,4-diyl moiety (to form together with the carbon atoms to which they are attached a benzene ring) optionally substituted by C$_{1-6}$alkyl.

When used herein alkyl means groups that are either straight-chained or branched. In general preferred alkyl groups are methyl and ethyl.

Suitably R$^1$ is aryl(C$_{1-6}$)alkyl such as phenyl(C$_{1-6}$)alkyl for example benzyl or phenethyl, heteroaryl(C$_{1-6}$)alkyl such as furanyl(C$_{1-6}$)alkyl or thienyl(C$_{1-6}$)alkyl for example furanylmethyl or thienylmethyl, halo(C$_{2-6}$)alkyl for example 2,2,2-trifluoroethyl, or C$_{3-10}$cycloalkyl for example cyclohexyl. More suitably R$^1$ is C$_{1-6}$alkyl, for example methyl, ethyl or propyl.

Suitably R$^2$ is hydrogen or C$_{1-6}$alkyl, for example methyl, ethyl or propyl.

Suitably R$^1$ and R$^2$ have the same value, for example they both are methyl or they are both ethyl. In another suitable aspect R$^1$ and R$^2$ together with the nitrogen atom to which they are attached form a pyrrolidino or piperidino ring.

Preferably n is one.

Suitably Z is 2,5-furanyl or 2,5-thienyl. In such compounds preferably Y is sulphur. For example R$^1$R$^2$N(CH$_2$)$_n$—Z—(CH$_2$)$_m$—Y—(CH$_2$)$_p$ may represent 5-dimethylaminomethylfuran-2-ylmethylthioethyl, 5-piperidinomethylfuran-2-ylmethylthioethyl or 5-pyrrolidinomethylfuran-2-ylmethylthioethyl.

In a preferred aspect Z is 2,4-pyridyl. In an alternative preferred aspect Z is 1,3-phenylene. In each type of compound suitably —(CH$_2$)$_m$Y—(CH$_2$)$_p$ is —CH$_2$SCH$_2$CH$_2$— and preferably —(CH$_2$)$_m$Y—(CH$_2$)$_p$ is —O—(CH$_2$)$_3$—. For example R$^1$R$^2$N(CH$_2$)$_n$—Z—(CH$_2$)$_m$—Y—(CH$_2$)$_p$— may represent:
4-dimethylaminomethylpyrid-2-ylmethylthioethyl,
4-piperidinomethylpyrid-2-ylmethylthioethyl,
4-dimethylaminomethylpyrid-2-yloxypropyl,
4-piperidinomethylpyrid-2-yloxypropyl,
3-dimethylaminomethylphenoxypropyl,
3-piperidinomethylphenoxypropyl,
3-dimethylaminomethylphenylmethylthioethyl or
3-piperidinomethylphenylmethylthioethyl.

In a particular aspect of this invention R$^3$ and R$^4$ independently represent hydrogen or C$_{1-6}$alkyl.

Suitably R$^3$ is hydrogen or C$_{1-6}$alkyl for example methyl, ethyl, propyl or butyl.

Suitably R$^4$ is hydrogen or C$_{1-6}$ for example methyl, ethyl, propyl or butyl.

Suitably R$^3$ and R$^4$ together represent a butadien-1,4-diyl moiety optionally substituted by C$_{1-6}$alkyl for example methyl. Favourably R$^3$ and R$^4$ represent an unsubstituted butadien-1,4-diyl moiety.

Favourably one of R$^3$ and R$^4$ is hydrogen. In a preferred aspect both R$^3$ and R$^4$ are hydrogen.

Suitably R$^5$ is hydrogen or methyl. In a preferred aspect R$^5$ is hydrogen.

A preferred group of compounds is that of the formula (I) wherein $R^3$, $R^4$ and $R^5$ are simultaneously hydrogen and X is oxygen.

The compounds of the formula (I), when $R^5$ is hydrogen, may exist in equilibrium with the following tautomeric forms:

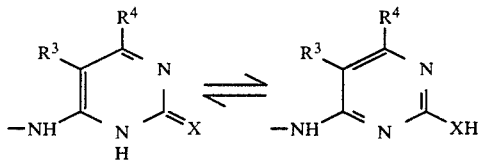

The activity of the compounds of formula (I) as histamine $H_2$-antagonists can be demonstrated by their ability to inhibit histamine-stimulated secretion of gastric acid from the lumen-perfused stomachs of rats anaesthetised with urethane, and to reverse histamine-induced inhibition of contractions of the isolated rat uterus. These are actions of histamine which, according to Ash and Schild, Brit. J. Pharmac. Chemother. 27 247 (1966), are not mediated by histamine $H_1$-receptors.

The histamine $H_2$-antagonist activity of the compounds can also be demonstrated by the inhibition of histamine-stimulated acid secretion in the Heidenhain Pouch Dog, the inhibition of histamine-induced tachycardia in the isolated guinea pig right atrium and the inhibition of histamine-induced vasodilatation in the anaesthetised cat.

The measurement of inhibition of histamine-stimulated secretion of gastric acid from the lumen-perfused stomachs of rats anaesthetised with urethane, and the measurement of inhibition of histamine-induced tachycardia in the isolated guinea pig right atrium, are detailed in European Patent Application Publication No. 0049173.

To illustrate the level of activity of the compounds of the invention we have determined that the products of the Examples 1-3 have $ED_{50}$ values in the lumen-perfused rat test of less than one micromol $kg^{-1}$ i.v. and $pA_2$ values in the guinea pig atrium test of more than seven.

In order to use compounds of the formula (I) or pharmaceutically acceptable salts thereof for medical purposes, they are normally formulated in accordance with standard pharmaceutical practice as pharmaceutical compositions.

The invention further provides pharmaceutical compositions comprising a compound of the formula (I) above or a pharmaceutically acceptable salt thereof together with a pharmaceutically acceptable carrier.

Compounds of the formula (I) and their pharmaceutically acceptable salts may be administered orally, parenterally, cutaneously or rectally.

Compounds of the formula (I) and their pharmaceutically acceptable salts which are active when given orally can be formulated as syrups, tablets, capsules and lozenges. A syrup formulation will generally consist of a suspension or solution of the compound or salt in a suitable liquid carrier for example, ethanol, glycerine or water with a flavouring or colouring agent. Where the composition is in the form of a tablet, any suitable pharmaceutical carrier routinely used for preparing solid formulations may be used. Examples of such carriers include magnesium stearate, starch, lactose, sucrose and cellulose.

Typical parenteral compositions consist of a solution or suspension of the compound of the formula (I) or pharmaceutically acceptable salt thereof in a sterile aqueous carrier or parenterally acceptable oil.

Typical compositions for administration to the skin include lotions and creams in which the compound of the formula (I) or pharmaceutically acceptable salt thereof is contained in a liquid vehicle.

A typical suppository formulation comprises a compound of the formula (I) or a pharmaceutically acceptable salt thereof which is active when administered in this way, with a binding and/or lubricating agent such as gelatin or cocoa butter or other low melting vegetable waxes or fats.

Preferably the composition is in unit dose form such as a tablet or capsule.

Each dosage unit for oral administration contains preferably from 15 to 250 mg (and for parenteral administration contains preferably from 0.5 to 25 mg) of a compound of formula (I) or a pharmaceutically acceptable salt thereof calculated as the free base.

The invention also provides a method of blocking histamine $H_2$ receptors which comprises administering to an animal an effective amount to block said receptors of a compound of formula (I) or a pharmaceutically acceptable salt thereof.

The compounds of the invention will normally be administered to a subject for the treatment of peptic ulcers and other conditions caused or exacerbated by gastric acidity in the same general manner as that employed for known histamine $H_2$-antagonists, due allowance being made in terms of dose levels for the potency of the compound of the present invention relative to known histamine $H_2$-antagonists. The daily dosage regimen for example for an adult patient may be an oral dose of between 15 mg and 1500 mg, preferably between 20 mg and 250 mg, or an intravenous, subcutaneous, or intramuscular dose of between 0.5 mg and 150 mg, preferably between 1 mg and 20 mg, of compound of the formula (I) or pharmaceutically acceptable salt thereof calculated as the free base, the composition being administered 1 to 6 times per day.

In a further aspect of this invention the compounds of the formula (I) and pharmaceutically acceptable salts thereof may be prepared by a process which comprises:

(a) reacting a compound of the formula (II) with a compound of the formula (III):

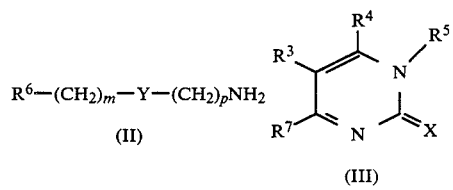

wherein $R^3$, $R^4$, $R^5$, m, p, X and Y are as hereinbefore defined, $R^6$ is a group $R^1R^2N(CH_2)_n-Z-$ as hereinbefore defined or $R^6$ is a furan-2-yl or thien-2-yl group and $R^7$ is a leaving group displaceable by amine; or (b) for compounds of the formula (I) wherein m is one and Y is sulphur, reacting a compound of the formula (IV) with a compound of the formula (V) or chemical equivalent thereof:

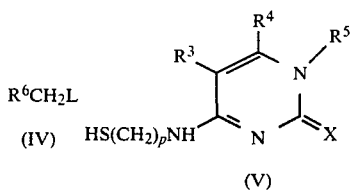

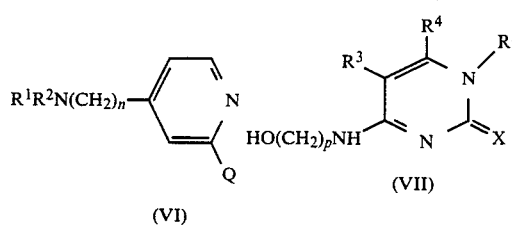

wherein $R^3$, $R^4$, $R^5$, $R^6$, X and p are as hereinbefore defined, and L is a moiety displaceable by thiol or chemical equivalent thereof; or (c) for compounds of the formula (I) wherein Z is 2,4-pyridyl, m is zero and Y is oxygen, reacting a compound of the formula (VI) with a compound of the formula (VII) or a derivative thereof that permits reaction to occur:

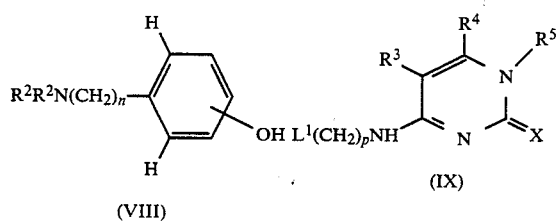

wherein $R^1$, $R^2$, $R^3$, $R^4$, $R^5$, X, n and p are as hereinbefore defined, and Q is a group displaceable by hydroxy or the equivalent thereof;

(d) for compounds of the formula (I) wherein Z is phenylene, m is zero and Y is oxygen, reacting a compound of the formula (VIII) or chemical equivalent thereof with a compound of the formula (IX):

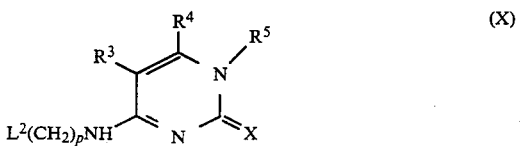

wherein $R^1$, $R^2$, $R^3$, $R^4$, $R^5$, X, n and p are as hereinbefore defined, and $L^1$ is a group displaceable by phenol or chemical equivalent thereof;

(e) for compounds of the formula (I) wherein m is one and Y is sulphur, reacting a compound of the formula (X):

wherein $R^3$, $R^4$, $R^5$, X, n and p are as hereinbefore defined, and $L^2$ is a group displaceable by thiol or chemical equivalent thereof, with a compound of the formula (XI) or chemical equivalent thereof:

$$R^6CH_2SH \qquad (XI)$$

wherein $R^6$ is as hereinbefore defined; or (f) converting a compound of the formula (XII):

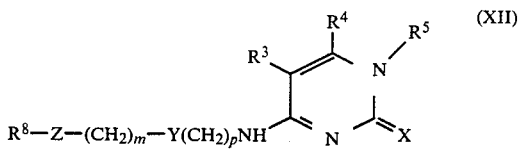

wherein Z, m, Y, p, X, $R^3$, $R^4$, and $R^5$, are as hereinbefore defined, and $R^8$ is a precursor of the group $R^1R^2N(CH_2)_n$ as hereinbefore defined; or (g) reducing a compound of the formula (XIII):

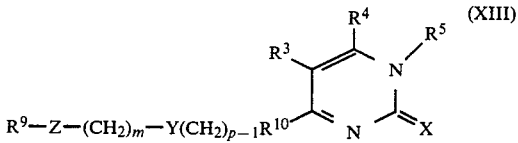

wherein Z, m, Y, p, X, $R^3$, $R^4$, and $R^5$, are as hereinbefore defined, $R^9$ is a group $R^6$ or $R^8$ as hereinbefore defined and $R^{10}$ is a group —CONH— or —CH=N—; and thereafter where necessary:

(i) wherein $R^5$ is hydrogen converting a compound of the formula (I) wherein X is sulphur to a compound of the formula (I) wherein X is oxygen;

(ii) reacting a compound wherein $R^6$ is furan-2-yl or thien-2-yl with a Mannich reagent to form a compound of the formula (I) wherein n is one;

(iii) converting a group $R^8$ to a group $R^1R^2N(CH_2)_n$-;

(iv) optionally forming a pharmaceutically acceptable salt.

The reaction between a compound of the formula (II) and a compound of the formula (III) can be performed in the absence of solvent at an elevated temperature or preferably in the presence of a substantially inert polar solvent. Suitably $R^7$ is mercapto and the reaction may be performed in a $C_{1-6}$alkanol or pyridine at reflux temperature or in an aprotic solvent such as dimethyl formamide at lower or ambient temperature. In an alternative $R^7$ may be $C_{1-6}$alkylthio, $C_{1-6}$alkoxy, chloro or bromo which may be displaced under similar conditions. A high boiling tertiary amine for example tri-n-propylamine, is useful when $R^7$ is chloro or bromo.

Examples of the moiety L include chloro, bromo, hydroxy, $C_{1-6}$alkoxy for example methoxy, $C_{1-6}$alkanoyloxy for example acetoxy, arylsulphonyloxy for example 4-methylbenzenesulphonyloxy, and $C_{1-6}$alkylsulphonyloxy for example methanesulphonyloxy.

Preferably L is hydroxy in which case the reaction between the compounds of the formulae (IV) and (V) is performed under acidic conditions. When L is chloro or bromo it is preferable to perform the reaction in the presence of a strong base for example sodium ethoxide in ethanol. When L is an arylsulphonyloxy or alkylsulphonyloxy group the reaction is preferably performed under mildly basic conditions for example in pyridine solution.

In the reaction of compounds of the formulae (IV) and (V), when carried out under basic conditions, when $R^5$ is hydrogen about one equivalent of base is used in order that a thiolate anion is preferentially formed on the $HS(CH_2)_pNH$-moiety. Alternatively X is protected during the reaction and thereafter deprotected in conventional manner. X for example may be protected as a hydrogenolysable group for example benzyl which may be removed in conventional manner.

Suitably in the compounds of the formula (VI), Q is chloro or bromo. The reaction of a compound of the formula (VI) with a compound of the formula (VII) is generally performed under basic conditions, for example the anion of the compound of the formula (VII) may be generated, for example using sodium hydride in a suitable solvent. In such reactions of compounds of the formulae (VI) and (VII) either $R^5$ is $C_{1-6}$alkyl or X is protected, so that a thiolate or alcoholate anion is not formed from the substituent X but rather an alcoholate anion is preferentially formed on the $HO(CH_2)_pNH$- moiety. X may thereafter be deprotected in conventional manner. X for example may be protected as a hydrogenolysable group for example benzyl which may be removed in conventional manner.

Suitably in the reaction of compounds of the formulae (VIII) and (IX) $L^1$ is chloro, bromo, arylsulphonyloxy for example 4-methylbenzenesulphonyloxy or $C_{1-6}$alkylsulphonyloxy for example methylsulphonyloxy. Such reactions are generally performed in the presence of base. Analogous considerations as to the nature of $R^5$ and X apply as in the case of the reactions of the compounds of the formulae (VI) and (VII). The reaction can be performed in a suitable aprotic solvent for example dimethylformamide at a non-extreme temperature for example between 0° C. and 100° C., suitably between ambient and 70° C.

Similarly in the reaction of the compounds of the formulae (X) and (XI) $L^2$ is chloro, bromo, arylsulphonyloxy for example 4-methylbenzenesulphonyloxy or $C_{1-6}$alkanesulphonyloxy for example methanesulphonyloxy. Such reactions are generally performed in the presence of base for example triethylamine, an alkoxide or a hydroxide. Analogous considerations as to the nature of $R^5$ and X apply as in the case of the reactions of the compounds of the formulae (VI) and (VII).

In the compounds of the formulae (XII) and (XIII) in one suitable aspect $R^8$ is a group $R^1R^2N(CH_2)_xCO(CH_2)_y$— wherein $x+y=n-1$. Favourably x and y are both zero so that the group $R^1R^2NCO$— is a precursor to the group $R^1R^2NCH_2$—. The conversion of such a group $R^1R^2N(CH_2)_x$—$CO(CH_2)_y$— may be performed by reduction for example with a hydride for example lithium aluminium hydride.

In an alternative aspect $R^8$ is a group $CHO$—$(CH_2)_{n-1}$— which may be converted to a group $R^1R^2N(CH_2)_n$- on reaction with an amine $R^1R^2NH$ under conditions of reductive amination. Furthermore in another suitable aspect $R^8$ may to be a group $HO(CH_2)_n$- which may be converted directly $R^1R^2N(CH_2)_n$— or indirectly thereto for example via a moiety such as $Br(CH_2)_n$— and thence to $R^1R^2N(CH_2)_n$—. Such transformations may be carried out in conventional manner.

The compounds of the formula (XIII) may be reduced for example using lithium aluminium hydride in an ether solvent when $R^{10}$ is —CONH—, and for example using a borohydride in an alcohol, lithium aluminium hydride in an ether solvent, or catalytically hydrogenating when $R^{10}$ is —CH=N—.

Compounds of the formula (I) wherein X is sulphur may be converted to the compounds of the formula (I) wherein X is oxygen via conventional methods of activating the sulphur atom and displacement. For example X may be converted to a $C_{1-6}$alkylsulphinyl group or a carboxymethylthio group (—$SCH_2COOH$) or an ester thereof which groups are subsequently treated with acid.

For converting a compound wherein $R^6$ is furan-2-yl or thien-2-yl to a compound of the formula (I) wherein n is one suitable Mannich reagents include formaldehyde and an amine $R^1R^2NH$ or salts thereof. Such a reaction may be carried out by treatment of an amine salt with aqueous formaldehyde and a compound wherein $R^6$ is furan-2-yl or thien-2-yl, or by refluxing an amine salt with paraformaldehyde and a compound wherein $R^6$ is furan-2-yl or thien-2-yl, in a convenient solvent such as ethanol. Alternatively where $R^1$ and $R^2$ are both $C_{1-4}$alkyl, the Mannich reagent may be a di-($C_{1-4}$alkyl)methylene ammonium salt for example dimethylmethylene ammonium chloride or iodide, or may be a bis di-$C_{1-4}$alkylaminomethane, for example bis(dimethylamino)methane.

Any group in the remainder of the molecule that is capable of reacting with a Mannich reagent may be optionally protected during the reaction, and may be subsequently deprotected in conventional manner.

It should be realised that compounds of the formula (I) wherein $R^3$ is hydrogen are capable of undergoing reaction with a Mannich reagent in that position, so that care should be taken to use approximately one equivalent of the Mannich reagent in such cases under suitably mild conditions.

The introduction of the group $R^1R^2N(CH_2)_n$- may be performed at any convenient stage of the synthetic procedures outlined herein or in the art. Such introduction may be direct or may involve two or more steps for example converting a hydroxymethyl substituent to bromomethyl and subsequently to $R^1R^2NCH_2$-.

Pharmaceutically acceptable acid addition salts of the compounds of the formula (I) may be prepared from the corresponding base of the compounds of the formula (I) in conventional manner. For example the base may be reacted with an acid in a $C_{1-4}$alkanol, or an ion-exchange resin may be used. The salts of the compounds of the formula (I) may be interconverted using ion-exchange resins. Non-pharmaceutically acceptable salts are therefore of use as they can be converted to pharmaceutically acceptable salts.

Suitable pharmaceutically acceptable acid addition salts of the compounds of the formula (I) include those formed with hydrochloric, hydrobromic, sulphuric, phosphoric, acetic, citric, maleic, lactic, ascorbic, fumaric, oxalic, methanesulphonic and ethanesulphonic acids.

The compounds of the formula (II) and (IV) may be prepared for example by the methods described in European Patent Application Publication Nos. 3677, 4793, 13071, 15138, 17679, 17680 and 49173 and UK Patent Application Publication No. 2030979A. The compounds of the formula (VI) may be prepared for example by the methods of European Patent Application Publication No. 49173.

The compounds of the formula (III) wherein X is sulphur and $R^7$ is mercapto may be prepared for example by the reacting phosphorus pentasulphide or Lawesson's reagent with a compound of the formula (XIV):

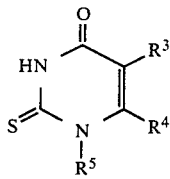

(XIV)

wherein $R^3$, $R^4$, and $R^5$, are as hereinbefore defined.

The compounds of the formula (III) wherein $R^7$ is alkoxy, and $R^5$ is alkyl may be prepared for example by the methods of J.C.S. 1955, p 855 Kenner et al.

The thiouracils of the formula (XIV) may be prepared by known methods, for example by reacting a thiourea with a β-oxoester of the formula (XV):

$$R^4COCHR^3CO_2R \qquad (XV)$$

wherein $R^3$, and $R^4$, are as hereinbefore defined and R is $C_{1-4}$alkyl.

Compounds of the formula (V) may be prepared by the reaction of a corresponding compounds of the formula (III) with an aminoalkylthiol wherein the thiol group is optionally protected, if desired. Compounds of the formula (VII) may be prepared by the reaction of the corresponding compounds of the formula (III) with an aminoalkanol. Compounds of formula (IX) and (X) may be prepared from compounds of the formula (III) by the reaction with $HO(CH_2)_pNH_2$ and subsequent replacement of HO by either a group $L^1$ or $L^2$. In such reactions the thiol or mercapto group or the $L^1$ or $L^2$ moiety or a reactive function X may be protected in conventional manner and subsequently deprotected. For example see European Patent Application Publication No. 24873 for protection of a thiol group.

The compounds of the formula (XII) may be prepared in a manner analogous to that described for the preparation of compounds of the formula (I), for example reacting a compound of the formula (III) with an analogue of a compound of the formula (II) wherein $R^6$ is replaced by $R^8$, provided that $R^8$ is suitably protected as necessary.

The compounds of the formula (XIII) wherein $R^{10}$ is —CH=N— may be prepared by the reaction of a compound of the formula (XVI) with a compound of the formula (XVII):

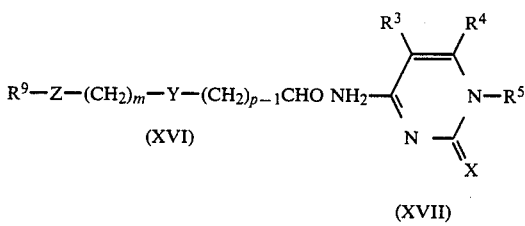

(XVI)                                (XVII)

wherein $R^9$, Z, m, Y, p, $R^3$, $R^4$, $R^5$ and X are as hereinbefore defined, optionally in the presence of an acid catalyst. The compounds of the formula (XIII) wherein $R^{10}$ is —CONH— may be prepared by the reaction of a compound of the formula (XVII) with an activated derivative of a compound of the formula (XVIII):

$$R^9-Z-(CH_2)_mY(CH_2)_{p-1}CO_2H \qquad (XVIII)$$

wherein $R^9$, Z, m, Y and p are as hereinbefore defined. Suitable active derivatives are acyl halides, anhydrides and activated esters. The aldehydes of the formula (XVI) may be prepared in conventional manner, for example by reacting a compound of the formula:

$$R^9-Z-OH$$

wherein $R^9$ and Z are as hereinbefore defined, with a protected bromopropionaldehyde (for example protected as a cyclic acetal) and deprotecting. The acid of the formula (XVIII) and derivatives thereof may be prepared in conventional manner, for example by reacting a compound of the formula: $R^9$—Z—OH with a protected bromopropionic acid and if necessary deprotecting and/or converting to the desired activated acid derivative.

The following Examples serve to illustrate the invention.

EXAMPLE 1

4-[3-(3-(Piperidinomethyl)phenoxy)propylamino]-pyrimidin-2-thione 3-(3-(Piperidinomethyl)phenoxy)propylamine (11.0 g) and dithiouracil (5.8 g) were refluxed in pyridine (100 ml; dried over potassium hydroxide) for approximately 72 hours. The solution was cooled and evaporated under reduced pressure to afford a residue. This residue was treated with water, evaporated under reduced pressure, and azeotroped thoroughly with n-propanol in an effort to remove pyridine. To the resultant residue was added further n-propanol to give the title compound as a solid which was collected by filtration and dried (13.88 g).

This solid was dissolved in N hydrochloric acid (100 ml), treated with charcoal, filtered and evaporated under reduced pressure with thorough azeotroping using n-propanol to give as a brown oil the dihydrochloride of the title compound (16.6 g).

A sample of the base obtained from another run of the procedure of the first paragraph was crystallised from acetone/methanol and recrystallised from methanol to afford 4-[3-(3-(piperidinomethyl)phenoxy)-propylamino]-pyrimidin-2-th ione, m.p. 180°–181° C.

EXAMPLE 2

4-[3-(3-(Piperidinomethyl)phenoxy)propylamino]-pyrimidin-2-one

4-[3-(3-(Piperidinomethyl)phenoxy)propylamino]-pyrimidin-2-thione dihydrochloride (16.5 g) and monochloroacetic acid (3.35 g) were dissolved in water (80 ml) and heated between steam bath and reflux temperature for approximately 4 hours. Concentrated hydrochloric acid (10 ml) was added and the mixture refluxed for 5 hours with further concentrated hydrochloric acid (10 ml, 10 ml) added after 2 hours and 4 hours.

The mixture was washed with ethyl acetate, taken to pH 9.5 with solid sodium carbonate and extracted into ethyl acetate (3 times). The latter ethyl acetate extracts were individually washed with water, dried and concentrated under reduced pressure. On leaving the first concentrated solution of ethyl acetate overnight, white crystals of the title compound (3.96 g) formed which were recrystallised from ethyl acetate/methanol, m.p. 159°–160° C. The second and third ethyl acetate extracts were combined and evaporated under reduced pressure to give on standing yellowish crystals of the title compound (6.31 g).

EXAMPLE 3

2-Oxo-4-[3-[3-(piperidinomethyl)phenoxy]-propylamino]-1,2-dihydroquinazoline 3-[3-(Piperidinomethyl)phenoxy]propylamine (2.98 g) and 2-oxo-4-thiono-1,2,3,4-tetrahydroquinazoline (1.78 g) (J. Heterocyclic Chem. 11 (5) p749 (1974)) were stirred in dimethylformamide (5 ml) for 5 days. The reaction mixture was filtered, washing through with cold dimethylformamide and diethyl ether. The filtrate was slowly evaporated to yield the title product as a white crystalline solid (1.38 g), m.p. 219°–221° C. (recrystallised from isopropanol).

EXAMPLE 4

2-Oxo-4-[3-[4-(piperidinomethyl)pyrid-2-yloxy]-propylamino]1,2-dihydroquinazoline 3-[4-(Piperidinomethyl)pyrid-2-yloxy]propylamine (2.03 g) and 2-oxo-4-thiono-1,2,3,4-tetrahydroquinazoline (1.24 g) were stirred in dimethylformamide (5 ml) at ambient temperature for 5 days. The reaction mixture was filtered to afford a solid that was washed with cold dimethylformamide and diethyl ether to yield the title product (1.25 g), m.p. 189°–192° C. (recrystallised from isopropanol).

EXAMPLE 5

By a method similar to that of Example 1 dithiouracil is reacted with:
(a) 2-(5-methylaminomethylthien-2-ylmethylthio)ethylamine,
(b) 2-(5-dimethylaminomethylfuran-2-ylmethylthio)ethylamine,
(c) 3-(3-pyrrolidinomethylphenoxy)propylamine,
(d) 3-(3-hexahydroazepinomethylphenoxy)propylamine,
(e) 4-(4-piperidinomethylphenoxy)butylamine,
(f) 2-(5-benzylaminomethylfuran-2-ylmethylthio)ethylamine,
(g) 2-(5-furan-2-ylmethylaminomethylfuran-2-ylmethylthio)ethylamine,
(h) 2-(5-thien-2-ylmethylaminomethylfuran-2-ylmethylthio)ethylamine,
(i) 2-(5-hydroxyethylaminomethylfuran-2-ylmethylthio)ethylamine,
(j) 2-(5-N-(2,2,2-trifluoroethyl)-N-methylaminomethylfuran-2-ylmethylthio)ethylamine,
(k) 2-(5-cyclohexylaminomethylfuran-2-ylmethylthio)ethylamine,
or an acid addition salt thereof to yield respectively:
(a) 4-[2-(5-methylaminomethylthien-2-ylmethylthio)ethylamino]pyrimidin-2-thione,
(b) 4-[2-(5-dimethylaminomethylfuran-2-ylmethylthio)ethylamino]pyrimidin-2-thione,
(c) 4-[3-(3-pyrrolidinomethylphenoxy)propylamino]pyrimidin-2-thione,
(d) 4-[3-(3-hexahydroazepinomethylphenoxy)propylamino]pyrimidin-2-thione,
(e) 4-[4-(4-piperidinomethylphenoxy)butylamino]pyrimidin-2-thione,
(f) 4-[2-(5-benzylaminomethylfuran-2-ylmethylthio)ethylamino]pyrimidin-2-thione,
(g) 4-[2-(5-furan-2-ylmethylaminomethylfuran-2-ylmethylthio)-ethylamino]pyrimidin-2-thione,
(h) 4-[2-(5-thien-2-ylmethylaminomethylfuran-2-ylmethylthio)-ethylamino]pyrimidin-2-thione,
(i) 4-[2-(5-hydroxyethylaminomethylfuran-2-ylmethylthio)ethylamino]pyrimidin-2-thione,
(j) 4-[2-(5-N-(2,2,2-trifluoroethyl)-N-methylaminomethyl-furan-2-ylmethylthio)ethylamino]pyrimidin-2-thione,
(k) 4-[2-(5-cyclohexylmethylaminomethylfuran-2-ylmethylthio)-ethylamino]pyrimidin-2-thione
or a pharmaceutically acceptable acid addition salt thereof.

Each of these products is converted into the corresponding pyrimidin-2-one by a method similar to that of Example 2.

EXAMPLE 6

A pharmaceutical composition for oral administration is prepared containing:

|   |   | % by weight |
|---|---|---|
| A | 4-[3-(3-piperidinomethylphenoxy)-propylamino]pyrimidin-2-one | 55 |
|   | Dibasic calcium phosphate dihydrate | 20 |
|   | Approved colouring agent | 0.5 |
|   | Polyvinylpyrrolidone | 4.0 |
| B | Microcrystalline Cellulose | 8.0 |
|   | Maize Starch | 8.0 |
|   | Sodium glycollate | 4.0 |
|   | Magnesium Stearate | 0.5 | by mixing together the ingredients A (substituting lactose or microcrystalline cellose for dibasic calcium phosphate dihydrate if desired), adding a concentrated solution of polyvinylpyrrolidone and granulating, drying and screening the dried granules; adding the ingredients B to the dried granules and compressing the mixture into tablets containing 100 mg, 150 mg or 200 mg of the free base.

Other compounds of the invention, for example those specifically described in Examples 1, 3 and 4 can be formulated into pharmaceutical compositions by a similar procedure.

The compounds of this invention, where tested, show no overt signs of toxicity at doses which are a pertinent multiple of the therapeutic dose.

What is claimed is:

1. A compound of the formula (I):

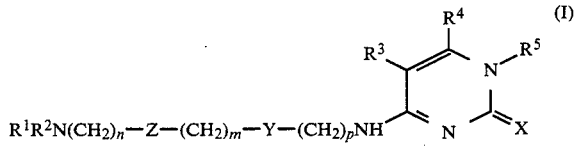

or a pharmaceutically acceptable salt thereof, wherein:
$R^1$ and $R^2$ are independently hydrogen, $C_{1-6}$alkyl, phenyl($C_{1-6}$)alkyl, furanyl($C_{1-6}$)alkyl, thienyl($C_{1-6}$)alkyl $C_{3-10}$cycloalkyl, hydroxy($C_{2-6}$)alkyl, halo($C_{2-6}$)alkyl (wherein said hydroxy and halo groups are not substituted on the carbon atom adjacent to the nitrogen atom); or
$R^1$ and $R^2$ together represent $-(CH_2)_q-$ wherein q is 4 to 7 to form together with the nitrogen atom to which they are attached a 5–8 membered saturated ring;
n is an integer from 1 to 6;
Z is 2,5-furanyl, 2,5-thienyl, 2,4-pyridyl wherein the $R^1R^2N(CH_2)_n$ group is in the 4-position, or 1,3- or 1,4-phenylene;

m is one; or if Z is pyridyl or phenylene m may also be zero;

Y is oxygen, sulphur or methylene; or if Z is furanyl or thienyl Y may also be a bond;

p is two, three or four;

X is oxygen or sulphur; and $R^3$, $R^4$ and $R^5$ independently represent hydrogen or $C_{1-6}$alkyl, or $R^3$ and $R^4$ together represent a butadien-1,4-diyl moiety (to form together with the carbon atoms to which they are attached a benzene ring) optionally substituted by $C_{1-6}$alkyl.

2. A compound according to claim 1 wherein $R^1R^2N(CH_2)_n-$ is piperidinomethyl.

3. A compound according to claim 1 wherein $R^1R^2N(CH_2)_nZ-(CH_2)_m-Y-(CH_2)_p$ is 3-dimethylaminomethylphenoxypropyl.

4. A compound according to claim 1 wherein $R^1R^2N(CH_2)_nZ-(CH_2)_m-Y-(CH_2)_p$ is 5-dimethylaminomethylfuran-2-ylmethylthioethyl.

5. A compound according to claim 1 wherein $R^1R^2N(CH_2)_nZ-(CH_2)_m-Y-(CH_2)_p$ is 3-piperidinomethylphenoxypropyl.

6. A compound according to claim 1 wherein $R^1R^2N(CH_2)_nZ-(CH_2)_m-Y-(CH_2)_p$ is 4-piperidinomethylpyrid-2-yloxypropyl.

7. A compound according to claim 1 wherein $R^1R^2N(CH_2)_nZ-(CH_2)_m-Y-(CH_2)_p$ is 4-piperidinomethylpyrid-2-ylmethylthioethyl.

8. A compound according to claim 1 wherein $R^1R^2N(CH_2)_nZ-(CH_2)_m-Y-(CH_2)_p$ is 5-pyrrolidinomethylfuran-2-ylmethylthioethyl.

9. A compound according to claim 1 wherein $R^1R^2N(CH_2)_nZ-(CH_2)_m-Y-(CH_2)_p$ is 4-dimethylaminomethylpyrid-2-ylmethylthioethyl.

10. A compound according to claim 1 wherein $R^1R^2N(CH_2)_nZ-(CH_2)_m-Y-(CH_2)_p$ is 3-dimethylaminomethylphenylmethylthioethyl.

11. A compound according to claim 1 wherein $R^1R^2N(CH_2)_nZ-(CH_2)_m-Y-(CH_2)_p$ is 4-dimethylaminomethylpyrid-2-yloxypropyl.

12. A compound according to claim 1 wherein $R^1R^2N(CH_2)_nZ-(CH_2)_m-Y-(CH_2)_p$ is 5-piperidinomethylfuran-2-ylmethylthioethyl.

13. A compound according to claim 1 wherein $R^5$ is hydrogen.

14. A compound according to claim 1 wherein $R^3$ and $R^4$ are each hydrogen.

15. A compound according to claim 1 wherein $R^3$ and $R^4$ together represent an unsubstituted butadien-1,4-diyl moiety.

16. A compound according to claim 1 which is 4-[3-(3-(piperidinomethyl)phenoxy)propylamino]pyrimidin-2-thione or a pharmaceutically acceptable salt thereof.

17. A compound according to claim 1 which is 4-[3-(3-(piperidinomethyl)phenoxy)propylamino]-pyrimidin-2-one or a pharmaceutically acceptable salt thereof.

18. A compound according to claim 1 which is 2-oxo-4-[3-[3-(piperidinomethyl)phenoxy]propylamino]-1,2-dihydroquinazoline or a pharmaceutically acceptable salt thereof.

19. A compound according to claim 1 which is 2-oxo-4-[3-[4-(piperidinomethyl)pyrid-2-yloxy]propylamino]1,2-dihydroquinazoline or a pharmaceutically acceptable salt thereof.

20. A pharmaceutical composition having histamine $H_2$-antagonist activity which comprises a compound according to claim 1 in an effective amount to produce said activity and a pharmaceutically acceptable carrier.

21. A method of blocking histamine $H_2$-receptors which comprises administering to a subject an effective amount to block said receptors of a compound according to claim 1.

* * * * *